United States Patent
Shirai et al.

(10) Patent No.: US 8,787,639 B2
(45) Date of Patent: Jul. 22, 2014

(54) MAGNETIC RESONANCE IMAGING DEVICE

(75) Inventors: Toru Shirai, Hachioji (JP); Yoshitaka Bito, Kokubunji (JP)

(73) Assignee: Hitachi Medical Corporation, Tokyo (JP)

( * ) Notice: Subject to any disclaimer, the term of this patent is extended or adjusted under 35 U.S.C. 154(b) by 60 days.

(21) Appl. No.: 13/577,355

(22) PCT Filed: Jan. 28, 2011

(86) PCT No.: PCT/JP2011/051785
§ 371 (c)(1),
(2), (4) Date: Aug. 6, 2012

(87) PCT Pub. No.: WO2011/108314
PCT Pub. Date: Sep. 9, 2011

(65) Prior Publication Data
US 2012/0301007 A1    Nov. 29, 2012

(30) Foreign Application Priority Data

Mar. 3, 2010  (JP) .................................. 2010-046073

(51) Int. Cl.
*G06K 9/00*  (2006.01)

(52) U.S. Cl.
USPC ....................................................... 382/128

(58) Field of Classification Search
CPC .... G06T 7/0012; G06T 7/0014; G06T 7/0016
USPC ................................................. 382/128–134
See application file for complete search history.

(56) References Cited

U.S. PATENT DOCUMENTS

| 2004/0010191 A1 | 1/2004 | Yatsui |
| 2010/0272337 A1* | 10/2010 | Shirai et al. ................... 382/131 |
| 2012/0051616 A1* | 3/2012 | Roland et al. ................. 382/131 |

FOREIGN PATENT DOCUMENTS

| JP | 11-225995 A | 8/1999 |
| JP | 2002-306441 A | 10/2002 |
| JP | 2006-149583 A | 6/2006 |

OTHER PUBLICATIONS

Dixon, W. Thomas; "Simple Proton Spectroscopic Imaging"; Radiology; Oct. 1984; vol. 153; pp. 189-194.

Reeder et al.; "Multicoil Dixon Chemical Species Separation With an Iterative Least-Squares Estimation Method"; Magnetic Resonance in Medicine; 2004; vol. 51; pp. 35-45.

(Continued)

*Primary Examiner* — Alex Liew
(74) *Attorney, Agent, or Firm* — Mattingly & Malur, PC

(57) ABSTRACT

Water/fat separation imaging is performed by an MRI device, even if the measurement is not performed with such echo times that the phases of water and fat signals become in-phase or out-of-phase. A determination is made as to which of two obtained separation images is a water image or a fat image. Two water/fat ratio maps are calculated from two original images obtained with such two echo times that phase differences of water and fat signals do not become positive and negative values, and do not becomes integral multiples of π. Two phase maps are calculated from the two water/fat ratio maps and are combined to calculate two minimum phase difference maps showing minimum spatial phase difference. From dispersion in differential maps obtained by spatially differentiating the minimum phase difference maps, a correct minimum phase difference map is determined, and is used to perform phase correction of the original image.

4 Claims, 10 Drawing Sheets

(56) References Cited

OTHER PUBLICATIONS

Ma, Jingfei; "Breath-Hold Water and Fat Imaging Using a Dual-Echo Two-Point Dixon Technique With an Efficient and Robust Phase-Correction Algorithm"; Magnetic Resonance in Medicine; 2004; vol. 52; pp. 415-419.

Takahashi et al.; "MRi Data Processing Technique in MRI: performance improvement on open MRI apparatus"; Medical Imaging Technology; Nov. 2001; vol. 19; No. 6; pp. 444-504.

* cited by examiner

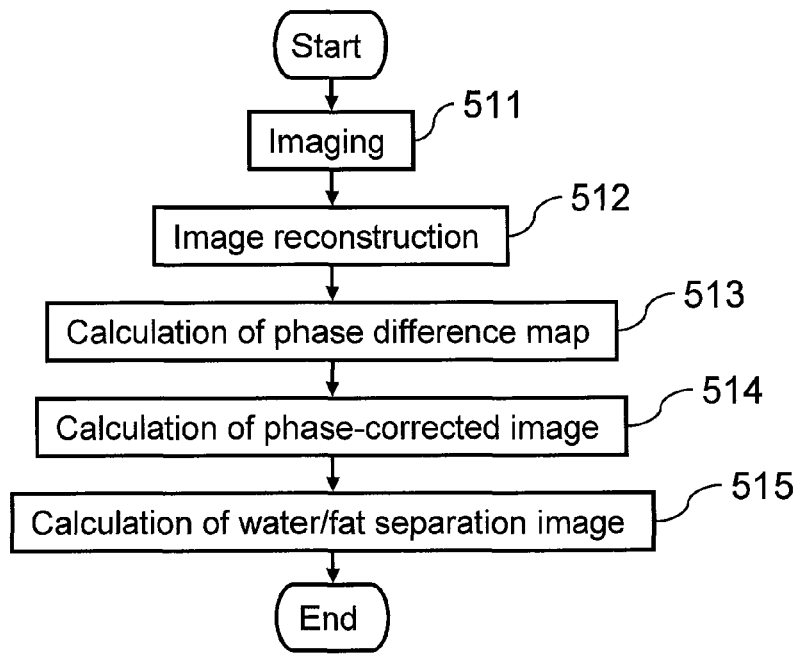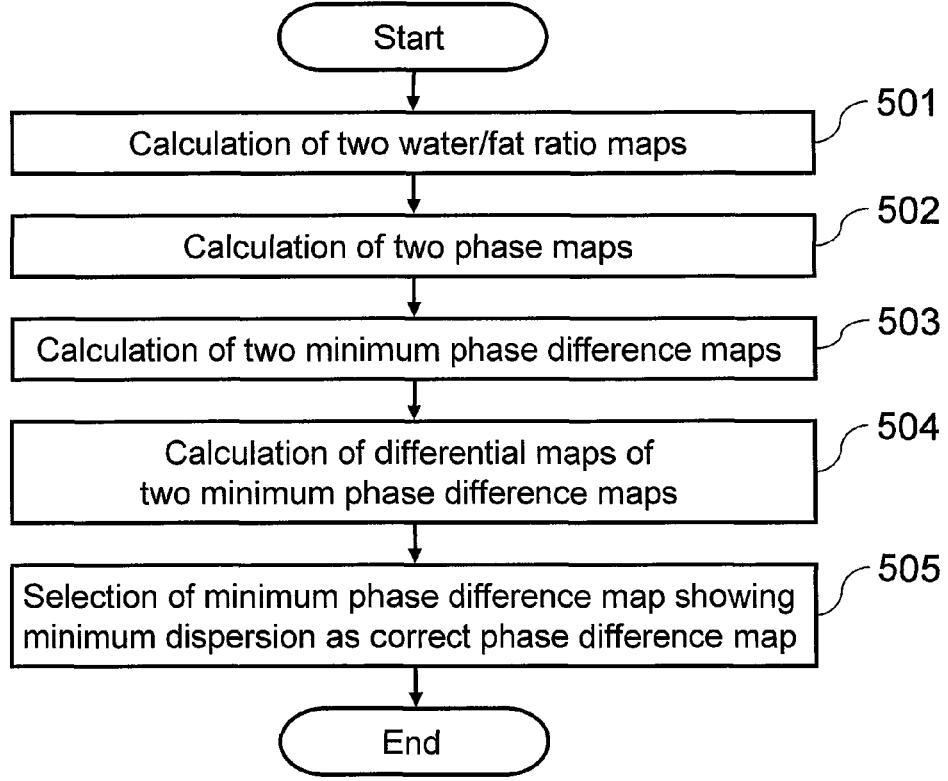

1001

MAGNETIC RESONANCE IMAGING DEVICE

TECHNICAL FIELD

The present invention relates to a magnetic resonance imaging device (henceforth referred to as MRI device), and in particular, it realizes favorable water/fat separation in water/fat separation imaging, even if the measurement is not performed with such an echo time that the phases of water and fat signals become in-phase or out-of-phase. The present invention further relates to a device and a method enabling distinction of obtained two separate images, i.e., to determine which is each of them, a water image or a fat image.

BACKGROUND ART

The currently most widely used nuclide for imaging in clinical MRI is hydrogen nucleus (proton), which is the major constituent of subjects.

MRI realizes two-dimensional or three-dimensional imaging of forms or functions of human head, abdominal part, limbs, and so forth by imaging spatial distribution of proton density or relaxation information of magnetic resonance signals.

When a human body is an object of the measurement, as the major sources of protons that can be detected by MRI, there are water and fats. Fats existing in human bodies reduce contrast of images of the abdominal part, spine, limbs, etc. of a subject.

Therefore, there have been proposed methods for suppressing fat signals in clinical measurements. As one of them, there is known the Dixon method (Non-patent document 1), in which fat signals are suppressed by using phase difference between water and fat signals.

Hereafter, the Dixon method will be explained.

Difference of "chemical shift", which indicates resonant frequency, between water and fats is 3.5 ppm, due to the difference in the molecular structures. The difference of the resonant frequency between water and fats is proportional to magnetic field strength, and when the magnetic field strength is 1.5 teslas, it corresponds to about 224 Hz.

The Dixon method utilizes the phase difference produced by the difference in the frequency of water and fats signals.

Data are obtained for a plurality of images with different times from excitation of nuclear spins to acquisition of signals (henceforth referred to as echo time). Specifically, images are obtained with such an echo time that water and fat signals become in-phase, and such an echo time that water and fat signals become out-of-phase.

When the frequency difference of water and fat signals is represented by df, such a time $t_{in}$ that the water and fat signals become in-phase is represented as n/df, and such a time $t_{out}$ that the water and fat signals become out-of-phase is represented as (n+½)/df, wherein n is an integer.

In the Dixon method, two of images, an image $I_1$ and an image $I_2$, are obtained with the echo times $t_{in}$ and $t_{out}$, respectively.

If a water signal is represented by W, and a fat signal is represented by F, $I_1$ and $I_2$ can be represented by the following equations (1) and (2), respectively.

$$I_1 = W + F \quad (1)$$

$$I_2 = W - F \quad (2)$$

By addition and subtraction of these equations for two images, the water signal and the fat signal are separated as represented by the following equations (3) and (4).

$$W = (I_1 + I_2)/2 \quad (3)$$

$$F = (I_1 - I_2)/2 \quad (4)$$

On the basis of the above, each of the water signal W and the fat signal F can be calculated, and separate images of water and fats can be obtained.

However, in the Dixon method, the phase rotation induced by inhomogeneity of the static magnetic field produced when a subject is inserted into the static magnetic field space is not taken into consideration. If spatial inhomogeneity of the static magnetic field exists, phase rotation is induced depending on the position, which is different from the chemical shift, and therefore there arises a problem that water and fats cannot be completely separated by the simple addition and subtraction as shown by the equations (3) and (4).

Therefore, as water/fat separation methods that take inhomogeneity of the static magnetic field into consideration, the methods described in Non-patent documents 2 and 3 are known.

Non-patent document 2 describes a method in which a least square estimation processing is repeatedly performed with three images obtained with different echo times to determine three variables, water signal W, fat signal F, and frequency difference f induced by inhomogeneity of the static magnetic field, to separate water and fats images.

In the method of Non-patent document 3, two of images, images $I_1$ and $I_2$, are obtained with such an echo time that water and fat signals become in-phase, and such an echo time that water and fat signals become out-of-phase, respectively, as in the Dixon method. However, in the method of Non-patent document 3, phase rotation induced by inhomogeneity of the static magnetic field is estimated by using the region growing method, and thereby water and fats signals are separated. In addition, in the method of Non-patent document 3, after the image $I_1$ is obtained with such an echo time $t_{in}$ that water and fat signals become in-phase, the gradient magnetic field pulse is reversed, and the image $I_2$ is obtained with such an echo time $t_{out}$ that water and fat signals become in-phase. That is, the in-phase image and out-of-phase image are obtained by one measurement.

PRIOR ART REFERENCES

Non-Patent Documents

Non-patent document 1: Thomas Dixon, et al., "Simple Proton Spectroscopic Imaging", Radiology, vol. 153, pages 189 to 194 (1984)

Non-patent document 2: Scott B. Reeder, et al., "Multicoil Dixon Chemical Species Separation With an Iterative Least-Squares Estimation Method", Magnetic Resonance in Medicine, vol. 51, pages 35 to 45 (2004)

Non-patent document 3: Jingfei Ma, "Breath-Hold Water and Fat Imaging Using a Dual-Echo Two-Point Dixon Technique With an Efficient and Robust Phase-Correction Algorithm", Magnetic Resonance in Medicine, vol. 52, pages 415 to 419 (2004)

SUMMARY OF THE INVENTION

Object to be Achieved by the Invention

In the method of Non-patent document 2 mentioned above, it is necessary to carry out the measurement three times, and therefore it has a problem that the measurement time is prolonged.

Further, in the method of Non-patent document 3, water and fat in-phase image and out-of-phase image are obtained by one measurement by reversing the gradient magnetic field pulse. However, the time interval dt of $t_{in}$ and $t_{out}$ is in inverse proportion to the magnetic field strength. For example, when the magnetic field strength is 3.0 teslas, dt is (1.12+2.24×n) ms, when the magnetic field strength is 1.5 teslas, dt is (2.24+4.48×n) ms, and when the magnetic field strength is 0.5 tesla, dt is (6.70+13.39×n) ms, wherein n is an integer.

Because dt is narrow at a magnetic field strength of 3.0 teslas or 1.5 teslas, the method suffers from restrictions concerning measurement, for example, the measurement band must be widened, and number of sampling points must be decreased. If the measurement band is widened, the SN ratio (henceforth abbreviated as SNR) is degraded, and thus image quality is degraded. If the number of sampling points is decreased, the spatial resolution of the image is degraded, and thus it becomes difficult to diagnose minute pathological lesions.

Since the time interval dt can be widened by adjusting the value of the integer n, the restrictions concerning measurement are eased to some extent. However, it is difficult to obtain an image with arbitrary contrast for both of the two images to be obtained.

When the magnetic field strength is 0.5 tesla, dt is large, and therefore the measurement time per one slice is prolonged. That is, in the two-dimensional multi-slice measurement, the number of slices per desired repetition time TR must be reduced, and therefore the number of slices desired to be obtained must also be decreased. Moreover, in the three-dimensional measurement, the measurement time is simply prolonged. If the measurement time is prolonged, motion artifacts of the subject increase. If the artifacts increase, errors in processing increase, and separation of water and fats signals becomes difficult.

Moreover, in human tissues in which water and fats are intermingled, water signals and fat signals are compensated with each other, and hence SNR of the out-of-phase image is lowered. Therefore, it becomes impossible to correctly calculate the phase rotation induced by inhomogeneity of the static magnetic field due to the noises. As a result, the errors in processing increase, and separation of water and fats signals becomes difficult.

Furthermore, it also suffers from the problem that it is difficult to determine a water image or a fat image from each of the obtained two images.

An object of the present invention is to realize favorable water/fat separation in water/fat separation imaging, even if the measurement is not performed with such an echo time that the phases of water and fat signals become in-phase or out-of-phase. A further object of the present invention is to realize a device and a method enabling distinction of obtained two separation images, i.e., determining which is each of them, a water image or a fat image.

Means for Achieving the Object

According to the present invention, two original images are measured with such two of echo times that phase differences of water and fat signals do not become positive and negative values, and do not become integral multiples of π. For example, when phase difference of water and fat signals obtained at a certain echo time $t_1$ is represented by $P_1$, and phase difference of water and fat signals obtained at an echo time $t_2$, which is dt after the echo time $t_1$, i.e., $t_1+dt=t_2$, is represented by $P_2$, the measurement is performed with such echo times $t_1$ and $t_2$ that the following equations are satisfied.

$$P_1 \neq n_1 \pi \text{ (}n_1 \text{ is an integer)} \tag{5}$$

$$P_2 \neq m_1 \pi \text{ (}m_1 \text{ is an integer)} \tag{6}$$

$$2n_2 \pi P_1 \neq -2m_2 \pi P_2 \text{ (}n_2 \text{ and } m_2 \text{ are integers)} \tag{7}$$

From two of the original images obtained under the aforementioned conditions, two of water/fat ratio maps are calculated algebraically or by numerical analysis. From two of the calculated water/fat ratio maps, two of phase maps are calculated. By combining two of the calculated phase maps, two of minimum phase difference maps, each of which gives the minimum spatial phase difference, are calculated. On the basis of dispersion in differential maps obtained by spatially differentiating the minimum phase difference maps, it is determined whether they are correct minimum phase difference maps. By using one of the phase difference maps determined to be correct, phase correction of one of the original images is performed. By using the corrected original image, water and fat separation processing is performed.

Specifically, the present invention provides a magnetic resonance imaging device comprising a static magnetic field generation part for generating a static magnetic field in a space in which a subject is placed, an irradiation part for irradiating a radio frequency magnetic field pulse on the subject, a reception part for receiving magnetic resonance signals generated from the subject by irradiation of the radio frequency magnetic field pulse, a gradient magnetic field application part for applying a gradient magnetic field for imparting spatial information to the magnetic resonance signals, a control part for operating the irradiation part, the gradient magnetic field application part, and the reception part according to a predetermined pulse sequence to perform imaging with two different echo times, and an image reconstruction part for reconstructing original images from the magnetic resonance signals obtained with the two different echo times, which further comprises a phase difference map calculation part for calculating maps of phase difference induced by inhomogeneity of the static magnetic field from the original images, a phase-corrected image calculation part for calculating a phase-corrected image by carrying out phase correction of one of the original images using the phase difference map, and a water/fat separation image calculation part for calculating a water/fat separation image from two images, the phase corrected image and the original image not subjected to the phase correction.

The aforementioned magnetic resonance imaging device measures original images, for example, at such two of echo times that the aforementioned equations (5), (6) and (7) are satisfied. The aforementioned phase difference map calculation part comprises, for example, a water/fat ratio calculation part for calculating two of water/fat ratio maps algebraically or by numerical analysis from two of the original images, a phase map calculation part for calculating two of phase maps from two of the water/fat ratio maps, a minimum phase difference map calculation part for calculating two of minimum phase difference maps from combinations of points on two of the phase maps so as to give a spatial minimum phase difference for each point, and a phase difference map determination part for determining whether two of the minimum phase difference maps are correct minimum phase difference maps on the basis of dispersion in differential maps obtained by spatially differentiating the minimum phase difference maps.

Effect of the Invention

According to the present invention, in a method of obtaining images with different echo times for separation of water and fats images, the restrictions concerning the measurement are eased, and favorable water/fat separation can be realized. Furthermore, it becomes possible to determine which is each of the obtained two images, a water image or a fat image.

BRIEF DESCRIPTION OF THE DRAWINGS

FIG. 5A shows a flowchart of a method for calculating images in which water and fats are separated in a magnetic resonance imaging device according to an embodiment of the present invention.

FIG. 5B shows a flowchart of a method for calculating phase difference map used in a magnetic resonance imaging device according to an embodiment of the present invention.

MODES FOR CARRYING OUT THE INVENTION

Hereafter, an embodiment of the MRI device of the present invention will be explained with reference to the drawings.

Figure 1A:
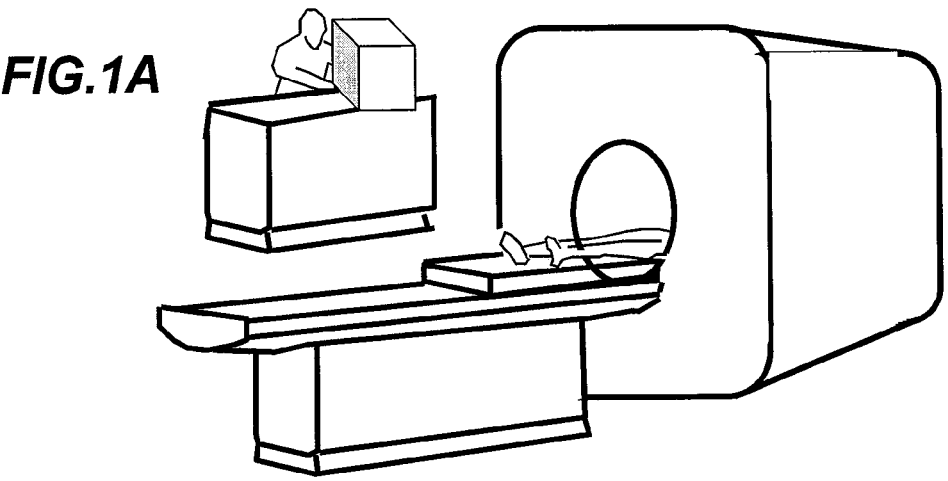
FIG. 1A shows an external view of an MRI device of the horizontal magnetic field type corresponding to embodiments of the present invention.
Figure 1B:
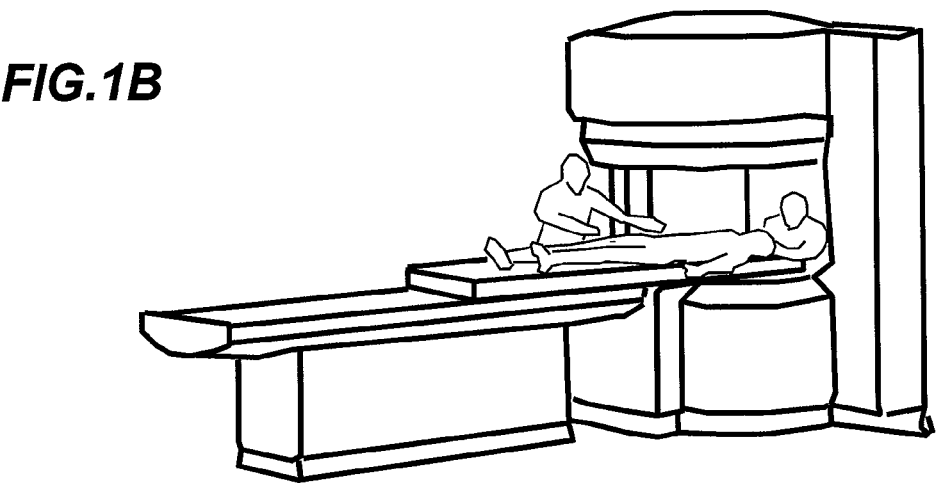
FIG. 1B shows an external view of an MRI device of the vertical magnetic field type corresponding to embodiments of the present invention.
Figure 1C:
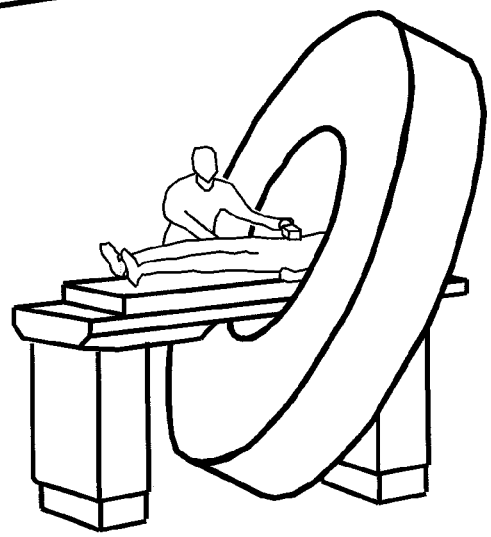
FIG. 1C shows an external view of another MRI device of the vertical magnetic field type corresponding to embodiments of the present invention.

FIG. 1A to FIG. 1C show total configurations and external views of magnetic resonance imaging devices corresponding to embodiments of the present invention. FIG. 1A shows an MRI device of the horizontal magnetic field type utilizing a tunnel-shaped magnet that generates a static magnetic field with a solenoid coil. FIG. 1B shows an MRI device of the vertical magnetic field type utilizing a hamburger type (open type) magnet having separated upper and lower magnets in order to increase spaciousness. Further, FIG. 1C shows a tunnel type MRI device similar to that of FIG. 1A, but depth of the magnet is shortened and the magnet is leaned to increase spaciousness. The present invention can be applied to MRI devices of known structures including MRI devices of these configurations, but the present invention is not limited to these, and can be applied regardless of the form and type of MRI devices.

Figure 2:
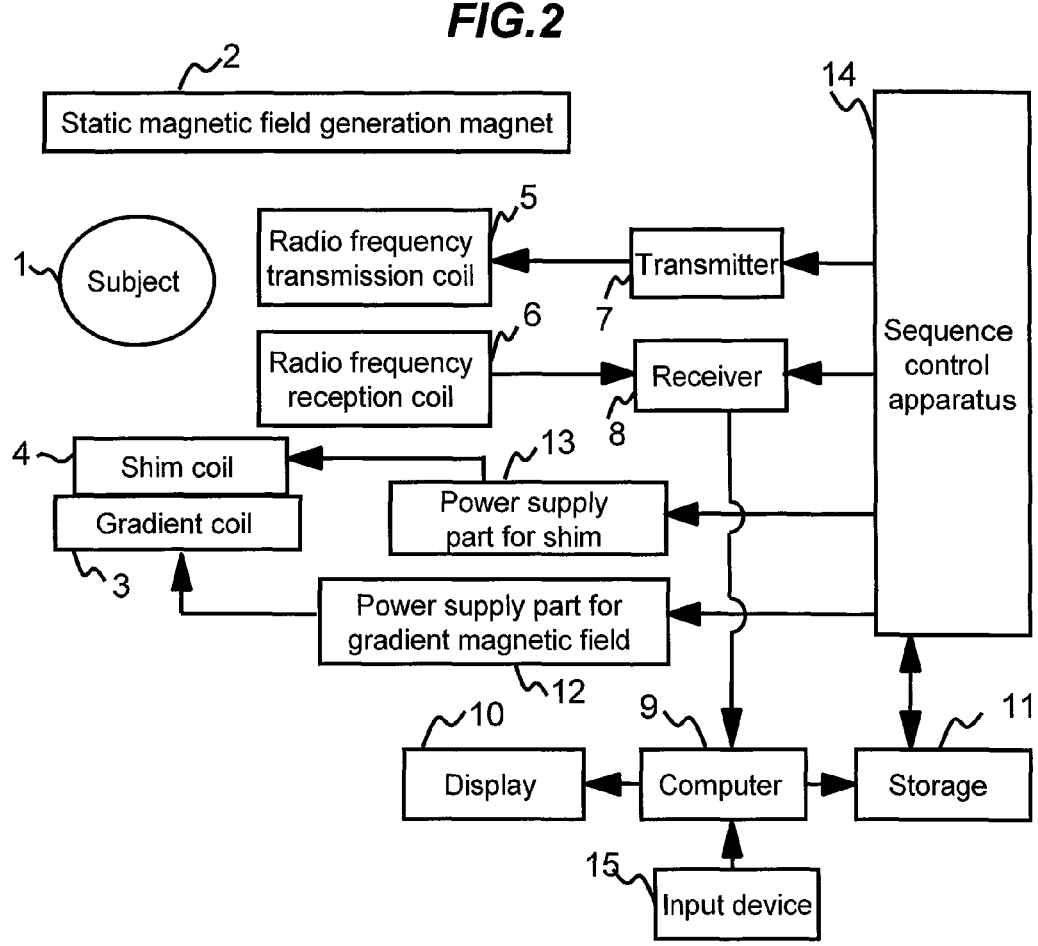
FIG. 2 shows an exemplary configuration of an MRI device according to an embodiment of the present invention.

FIG. 2 shows an exemplary configuration of an MRI device according to this embodiment. This MRI device is provided with a static magnetic field generation magnet 2 that generates a static magnetic field in a space in which a subject 1 is placed, a gradient coil 3 for applying gradient magnetic fields for three directions perpendicular to each other in the static magnetic field, a shim coil 4 that can control homogeneity of the static magnetic field, a radio frequency coil 5 for measurement (henceforth referred to simply as transmission coil) that irradiates a radio frequency magnetic field on a measurement region of the subject 1, and a radio frequency coil 6 for reception (henceforth referred to simply as reception coil) that receives magnetic resonance signals generated from the subject 1.

The static magnetic field generation magnet 2 is chosen from those having various forms according to the structure of the device shown in FIG. 1. The gradient coil 3 and the shim coil 4 are driven by a power supply part 12 for gradient magnetic field and a power supply part 13 for shim, respectively. Although the transmission coil 5 and the reception coil 6 are separately shown in FIG. 2, only one radio frequency coil serving as both transmission and reception coils may also be used. The radio frequency magnetic field irradiated by the transmission coil 5 is generated by a transmitter 7. The magnetic resonance signals detected by the reception coil 6 are sent to a computer 9 via a receiver 8.

The computer 9 performs various processings of the magnetic resonance signals, and generates image information and so forth. The aforementioned processings include various processings for calculating water and fat separation images.

A display 10, a storage 11, an input device 15, and so forth are connected to the computer 9. For example, the aforementioned image information or information of an imaging region is displayed on the display 10, or recorded in the storage 11. The input device 15 is for inputting measurement conditions, conditions required for the processings, and so forth, and these measurement conditions and so forth are also recorded in the storage 11 as required.

A sequence control apparatus 14 controls the power supply part 12 for gradient magnetic field for driving the gradient coil 3, the power supply part 13 for shim for driving the shim coil 4, the transmitter 7, and the receiver 8. A time chart of the control (pulse sequence) is determined beforehand according to the imaging method, and is stored in the storage 11.

Figure 3:
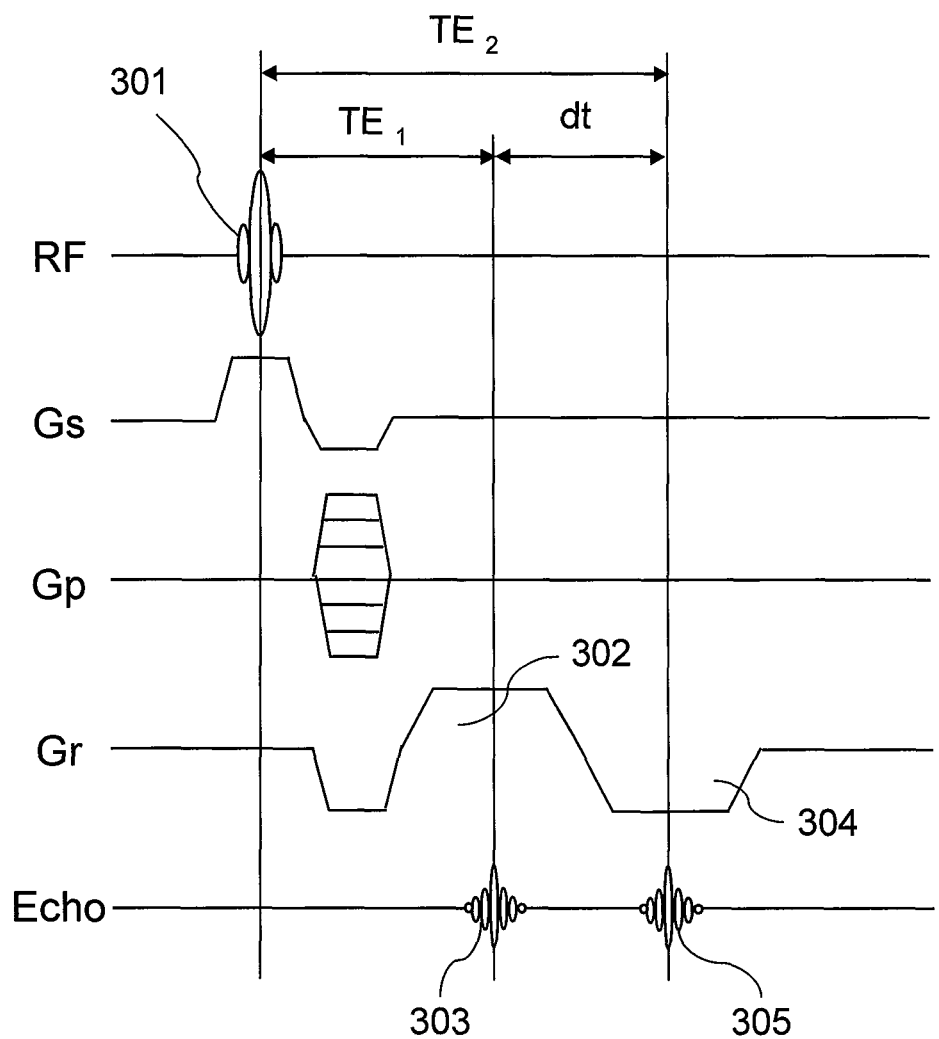
FIG. 3 shows an example of gradient echo pulse sequence used in an MRI device according to an embodiment of the present invention.

The pulse sequence executed in the MRI device of this embodiment will be explained below. A time chart of a pulse sequence employed in this embodiment is shown in FIG. 3. In this pulse sequence, an RF pulse 301 is first irradiated to excite spins in the subject. At the same time, a slice selection gradient magnetic field Gs is applied simultaneously with the RF pulse 301 for selection of a specific slice of the subject. Then, a phase encoding gradient magnetic field Gp for phase encoding of the magnetic resonance signals is applied, then a read-out gradient magnetic field Gr 302 is applied, and after a time of $TE_1$ from the irradiation of the first RF pulse 301, an echo signal (first echo) 303 is measured. Further, a read-out gradient magnetic field Gr 304 of reversed polarity is applied, and after a time of dt from the measurement of the first echo 303, an echo signal (second echo) 305 is measured. The echo time $TE_2$ of this measurement is written as follows: $TE_2=TE_1+dt$.

The echo time $TE_1$ for measuring the first echo 303 and the echo time $TE_2$ for measuring the second echo 305 are chosen so that the conditions of the following equations (5), (6) and (7) are satisfied. That is, when phase difference of water and fat signals obtained at the echo time $TE_1$ is represented by $P_1$, and phase difference of water and fat signals obtained at an echo time $TE_2$, dt after the echo time $TE_1$, i.e., $TE_1+dt=TE_2$, is represented by $P_2$, the echo times $TE_1$ and $TE_2$ are selected so that the following equations are satisfied.

$$P_1 \neq n_1\pi \text{ ($n_1$ is an integer)} \quad (5)$$

$$P_2 \neq m_1\pi \text{ ($m_1$ is an integer)} \quad (6)$$

$$2n_2\pi P_1 \neq -2m_2\pi P_2 \text{ ($n_2$ and $m_2$ are integers)} \quad (7)$$

As described above, according to this embodiment, the echo times $TE_1$ and $TE_2$ are determined so that the phase difference of water and fat signals are not positive and negative nor vice versa, as indicated by the equation (7). Further, the echo times $TE_1$ and $TE_2$ are determined so that the phase differences $P_1$ and $P_2$ of water and fat signals do not become an integral multiple of $\pi$, as indicated by the equations (5) and (6).

This sequence is repeated for a predetermined number of times with changing the intensity of the phase encoding gradient magnetic field Gp. For example, echo signals are repeatedly obtained for a number of times required for image reconstruction, such as 128 times or 256 times. And one image (first echo image) is reconstructed from the first echoes 303 in the number of the repetition times, and another image (second echo image) is reconstructed from the second echoes 305 in the number of the repetition times. These are used as images for calculating water image and fat image described later.

Figure 4:
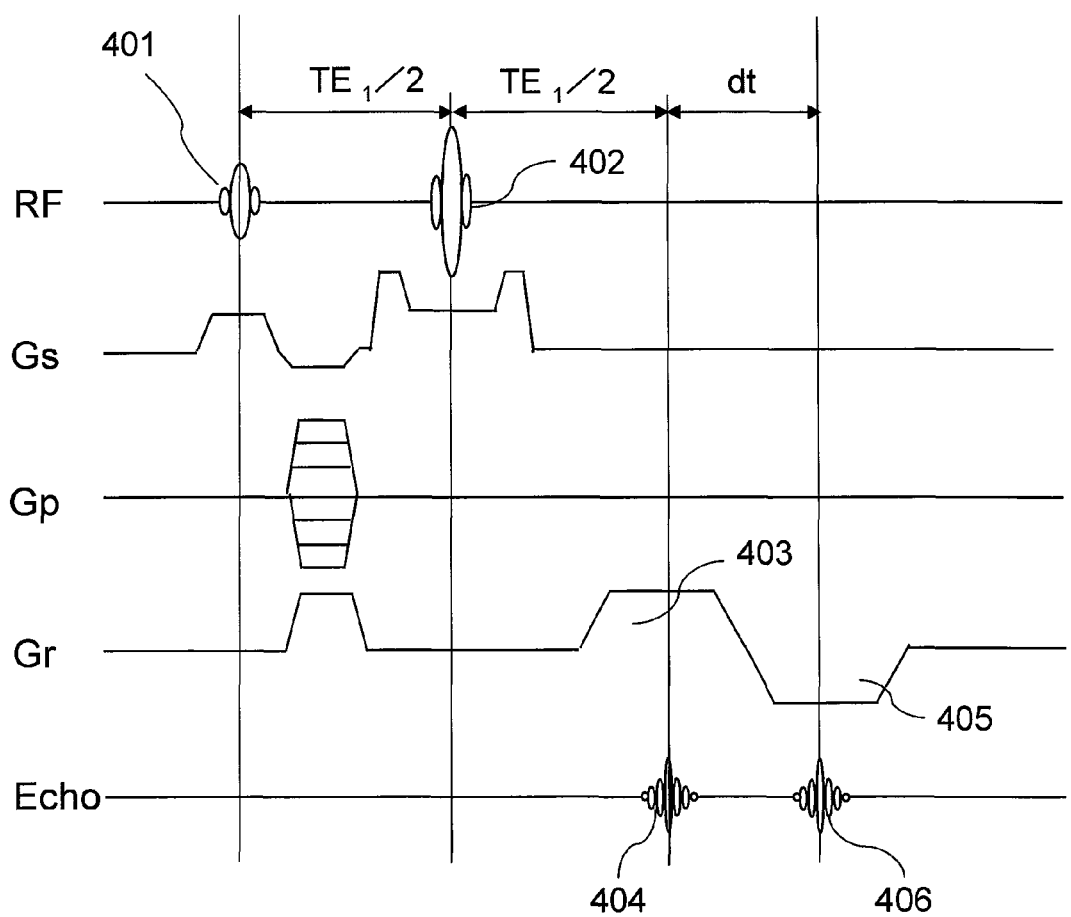
FIG. 4 shows an example of spin echo pulse sequence used in an MRI device according to an embodiment of the present invention.

Although a gradient echo pulse sequence is shown in FIG. 3, the pulse sequence may be such a spin echo pulse sequence as shown in FIG. 4.

A spin echo pulse sequence is shown in FIG. 4. With this pulse sequence, an RF pulse 401 is first irradiated to excite spins in the subject. At the same time, a slice selection gradient magnetic field Gs is applied simultaneously with the RF pulse 401 for selection of a specific slice of the subject. Then, a phase encoding gradient magnetic field Gp for phase encoding of the magnetic resonance signals is applied, and an RF pulse 402 for reversing the spins is further irradiated together with the slice selection gradient magnetic field Gs. Then, a read-out gradient magnetic field Gr 403 is applied, and after the time of $TE_1$ from the irradiation of the first RF pulse 401, an echo signal (first echo) 404 is measured. Further, a read-out gradient magnetic field Gr 405 of reversed polarity is applied, and after the time of dt from the measurement of the first echo 404, an echo signal (second echo) 406 is measured.

The echo time $TE_1$ for measuring the first echo 404 and the echo time $TE_2$ for measuring the second echo 406 are chosen so that the conditions of the equations (5), (6) and (7) are satisfied, as in the case of the gradient echo pulse sequence.

For both the gradient echo pulse sequence and the spin echo pulse sequence, two signals may be measured at different echo times within one repetition time as shown in FIGS. 3 and 4, or signals may be measured at different echo times by two times of measurement.

In this embodiment, as shown in FIG. 5A, water/fat separation images are calculated. That is, the parts are respectively controlled by the sequence control apparatus 14 to execute the pulse sequence shown in FIG. 3 or 4 mentioned above and thereby obtain echo signals at the different times $TE_1$ and $TE_2$ (imaging, Step 511). And in the computer 9, original images are reconstructed from the echo signals obtained at the different times $TE_1$ and $TE_2$ (image reconstruction, Step 512).

Then, in the computer 9, maps of phase difference induced by inhomogeneity of the static magnetic field are calculated from two of the original images obtained in Step 512 (calculation of phase difference map, Step 513). By using the obtained phase difference maps, one of the two original images obtained in Step 512 is corrected (calculation of phase-corrected image, Step 514), and from the corrected image and the original image not corrected in Step 514, water/fat separation images are calculated (calculation of water/fat separation image, Step 515).

The procedure for calculating the maps of phase difference induced by inhomogeneity of the static magnetic field in the magnetic resonance imaging device of this embodiment in Step 513 mentioned above will be explained with reference to FIG. 5B.

In Step 501, two of water/fat ratio maps are calculated. First, equations for calculating the water/fat ratio maps are obtained. If phase of water signal at the echo time $t_1$ at which the first echo is measured is represented as $\sigma_{W1}$, phase of fat signal at the echo time $t_1$ is represented as $\sigma_{F1}$, phase rotation induced by inhomogeneity of the static magnetic field at the echo time $t_1$ is represented as $\delta_1$, phase of water signal at the echo time $t_2$ at which the second echo is measured is represented as $\sigma_{W2}$, phase of fat signal at the echo time $t_2$ is represented as $\sigma_{F2}$, phase rotation induced by inhomogeneity of the static magnetic field at the echo time $t_2$ is represented as $\delta_2$, initial phase is represented as $\Phi$, absolute value of the signal obtained as the first echo is represented as $r_1$, angle of deviation of the signal is represented as $\theta_1$, absolute value of the signal obtained as the second echo is represented as $r_2$, angle of deviation of the signal is represented as $\theta_2$, rate of water signals included in a voxel is represented as $R_W$, rate of fat signals included in the voxel is represented as $R_F$, and constant of proportionality is represented as k, the first and second echoes are represented by the equations (8) and (9), respectively.

$$k \cdot \{R_W \cdot \exp(i\sigma_{W1}) + R_F \cdot \exp(i\sigma_{F1})\} \cdot \exp(i\delta_1) \cdot \exp(i\phi) = r_1 \cdot \exp(i\theta_1) \quad (8)$$

$$k \cdot \{R_W \cdot \exp(i\sigma_{W2}) + R_F \cdot \exp(i\sigma_{F2})\} \cdot \exp(i\delta_2) \cdot \exp(i\phi) = r_2 \cdot \exp(i\theta_2) \quad (9)$$

Next, the sides of the equation (9) are divided with the sides of the equation (8), respectively, to obtain the equation (10).

$$\frac{R_W \cdot \exp(i\sigma_{W2}) + R_F \cdot \exp(i\sigma_{F2})}{R_W \cdot \exp(i\sigma_{W1}) + R_F \cdot \exp(i\sigma_{F1})} \cdot \exp(i\delta) = r \cdot \exp(i\theta) \quad (10)$$

In the equation, $\delta=\delta_2-\delta_1$, $r=r_2/r_1$, and $\theta=\theta_2-\theta_1$.

Next, squares of the absolute values of both sides of the equation (10) are obtained.

$$\left|\frac{R_W \cdot \exp(i\sigma_{W2}) + R_F \cdot \exp(i\sigma_{F2})}{R_W \cdot \exp(i\sigma_{W1}) + R_F \cdot \exp(i\sigma_{F1})}\right|^2 = r^2 \quad (11)$$

Then, such a condition for making the sum of the rates $R_W$ and $R_F$ of water signals and fat signals included in a voxel constant is added. For example, it is assumed that $R_W$ and $R_F$ satisfy the relation represented by the equation (12).

$$R_W + R_F = 1 \qquad (12)$$

From the equations (11) and (12), the following equations (13) and (14) are obtained.

$$R_W = \frac{A \pm \sqrt{A \cdot B}}{2A} \qquad (13)$$

$$R_F = \frac{A \mp \sqrt{A \cdot B}}{2A} \qquad (14)$$

A and B in the equations are written by the following equations (15) and (16).

$$A = r^2 \cdot \cos(\sigma_{W1} - \sigma_{F1}) - \cos(\sigma_{W2} - \sigma_{F2}) + (1 - r^2) \qquad (15)$$

$$B = r^2 \cdot \cos(\sigma_{W1} - \sigma_{F1}) - \cos(\sigma_{W2} - \sigma_{F2}) - (1 - r^2) \qquad (16)$$

All of $\sigma_{W1}$, $\sigma_{F1}$, $\sigma_{W2}$ and $\sigma_{F2}$ are known values, and r can be calculated from the two measured original images. Therefore, two water/fat ratio maps, $R_{W+}:R_{F+}$ and $R_{W-}:R_{F-}$, can be calculated from the equations (13) to (16) as written in the following equations (17) and (18). When the rate of water signals $R_W$ is positive, it is represented as $R_{W+}$, and $R_F$ calculated in accordance with the equation (12) is represented as $R_{F+}$. Further, when the ratio of water signals $R_W$ is negative, it is represented as $R_{W-}$, and $R_F$ calculated in accordance with the equation (12) is represented as $R_{F-}$.

$$R_{W+}:R_{F+} = \frac{A + \sqrt{A \cdot B}}{2A} : \frac{A - \sqrt{A \cdot B}}{2A} \qquad (17)$$

$$R_{W-}:R_{F-} = \frac{A - \sqrt{A \cdot B}}{2A} : \frac{A + \sqrt{A \cdot B}}{2A} \qquad (18)$$

$R_{W+}$, $R_{F+}$, $R_{W-}$ and $R_{F-}$ may also be obtained from the equations (11) and (12) by numerical analysis. That is, $R_{W+}$, $R_{F+}$, $R_{W-}$ and $R_{F-}$ may be obtained by changing $R_W$ in the left side of the equation (11) from 0 to 1 (changing $R_F$ from 1 to 0) with satisfying the relation of the equation (12) to search for a combination of them providing the smallest difference with respect to the absolute value r obtained after the complex division.

Next, in Step 502, two of phase maps, $\delta_+$ and $\delta_-$, are calculated from two of the water/fat ratio maps calculated in Step 501. The phase map calculated from $R_{W+}$ and $R_{F+}$ is defined as $\delta_+$, and the phase map calculated from $R_{W-}$ and $R_{F-}$ is defined as $\delta_-$.

When $\sigma_{F1}$ is in the range of 0 to $\pi$, $\delta_+$ represents a correct static magnetic field map in the region in which water signals constitute the main component, and $\delta_-$ represents a correct static magnetic field map in the region in which fat signals constitute the main component, as described below. On the other hand, when $\sigma_{F1}$ is in the range of $-\pi$ to 0, $\delta_+$ represents a correct static magnetic field map in the region in which fat signals constitute the main component, and $\delta_-$ represents a correct static magnetic field map in the region in which water signals constitute the main component.

$\sigma_{W1}$, $\sigma_{F1}$, $\sigma_{W2}$, $\sigma_{F2}$, $R_{W+}$ and $R_{F+}$ are substituted for the equation (10) to obtain the equations (19) to (21).

$$s_+ \cdot \exp(i\omega_+) \cdot \exp(i\delta) = r \cdot \exp(i\theta) \qquad (19)$$

$$s_+ = \left| \frac{R_{W+} \cdot \exp(i\sigma_{W2}) + R_{F+} \cdot \exp(i\sigma_{F2})}{R_{W+} \cdot \exp(i\sigma_{W1}) + R_{F+} \cdot \exp(i\sigma_{F1})} \right| \qquad (20)$$

$$\omega_+ = \arg\left(\frac{R_{W+} \cdot \exp(i\sigma_{W2}) + R_{F+} \cdot \exp(i\sigma_{F2})}{R_{W+} \cdot \exp(i\sigma_{W1}) + R_{F+} \cdot \exp(i\sigma_{F1})}\right) \qquad (21)$$

Further, $\sigma_{W1}$, $\sigma_{F1}$, $\sigma_{W2}$, $\sigma_{F2}$, $R_{W-}$ and $R_{F-}$ are substituted for the equation (10) to obtain the equations (22) to (24).

$$s_- \cdot \exp(i\omega_-) \cdot \exp(i\delta) = r \cdot \exp(i\theta) \qquad (22)$$

$$s_- = \left| \frac{R_{W-} \cdot \exp(i\sigma_{W2}) + R_{F-} \cdot \exp(i\sigma_{F2})}{R_{W-} \cdot \exp(i\sigma_{W1}) + R_{F-} \cdot \exp(i\sigma_{F1})} \right| \qquad (23)$$

$$\omega_- = \arg\left(\frac{R_{W-} \cdot \exp(i\sigma_{W2}) + R_{F-} \cdot \exp(i\sigma_{F2})}{R_{W-} \cdot \exp(i\sigma_{W1}) + R_{F-} \cdot \exp(i\sigma_{F1})}\right) \qquad (24)$$

Since $s_+ = s_- = r$, the desired phase maps $\delta_+$ and $\delta_-$ can be obtained as written in the following equations (25) and (26), respectively.

$$\delta_+ = \theta - \omega_+ \qquad (25)$$

$$\delta_- = \theta - \omega_- \qquad (26)$$

Then, in Step 503, two minimum phase difference maps giving a minimum spatial phase change at each point in the two phase maps are calculated. The procedure therefor will be explained by using a model.

First, the chemical shift of water $f_W$ is defined to be 0 Hz, the chemical shift of fat $f_F$ is defined to be 224 Hz, and it is supposed that there is no inhomogeneity of the static magnetic field for simplicity. And there is supposed a one-dimensional model constituted with regions arranged in a line, in which the ratios of water and fat are 0:100, 25:75, 50:50, 75:25 and 100:0.

With the above model, the following four patterns (A) to (D) of the conditions of the echo time $t_1$ for the first echo and the echo time $t_2$ for the second echo are compared.

(A) $t_1$: 4.5 ms (in phase), $t_2$: 6.0 ms
(B) $t_1$: 6.7 ms (out of phase), $t_2$: 8.2 ms
(C) $t_1$: 4.5 ms (in phase), $t_2$: 6.7 ms (out of phase)
(D) $t_1$: 6.7 ms (out of phase), $t_2$: 8.9 ms (in phase)

In the aforementioned conditions, in phase means that, at that echo time, phase difference of water and fat signals is 0, and out of phase means that, at that echo time, phase difference of water and fat signals is $\pi$. The conditions (A) and (B) are conditions of this embodiment, and the conditions (C) and (D) are conventionally used conditions.

In addition, although the phase difference of water and fat signals for the echo time of $t_1$ is 0 in the condition (A), the phase difference may not be 0 so long as the conditions of the equations (5) to (7) are satisfied. Further, although the phase difference of water and fat signals for the echo time of $t_1$ is $\pi$ in the condition (B), the phase difference may not be $\pi$ so long as the conditions of the equations (5) to (7) are satisfied.

Figure 6A:
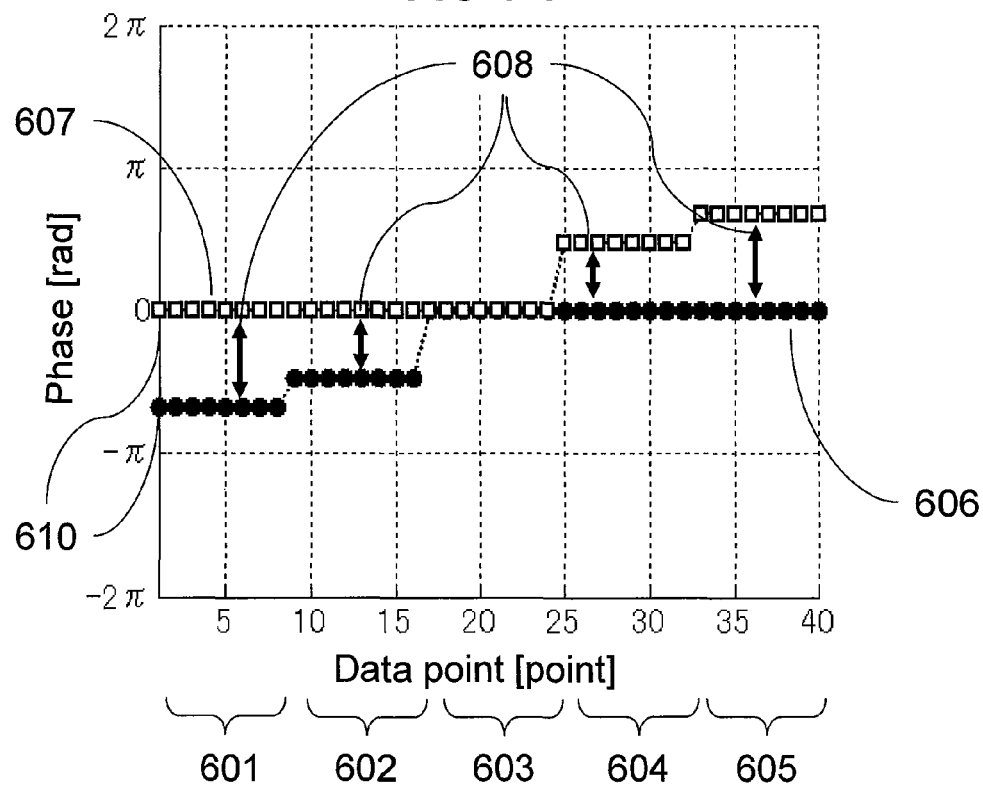
FIG. 6A is a diagram for explaining two of phase maps obtained with the measurement conditions used in a magnetic resonance imaging device according to an embodiment of the present invention.
Figure 6B:
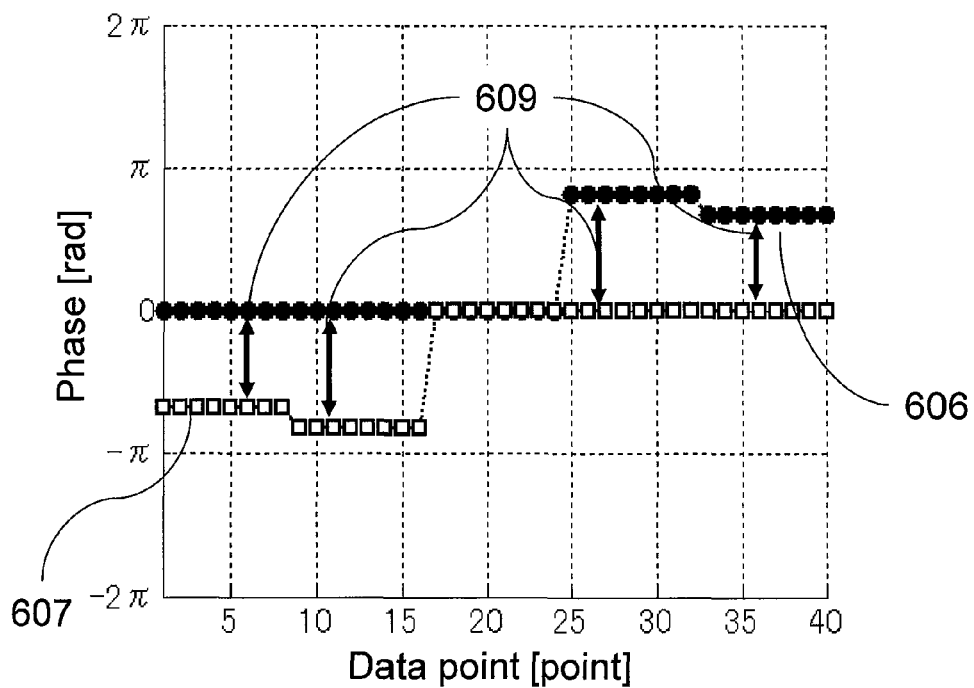
FIG. 6B is a diagram for explaining two of phase maps obtained with the measurement conditions used in a magnetic resonance imaging device according to an embodiment of the present invention.

The phase maps $\delta_+$ and $\delta_-$ for the condition (A) are shown in FIG. 6A, and the phase maps $\delta_+$ and $\delta_-$ for the condition (B) are shown in FIG. 6B.

Figure 7A:
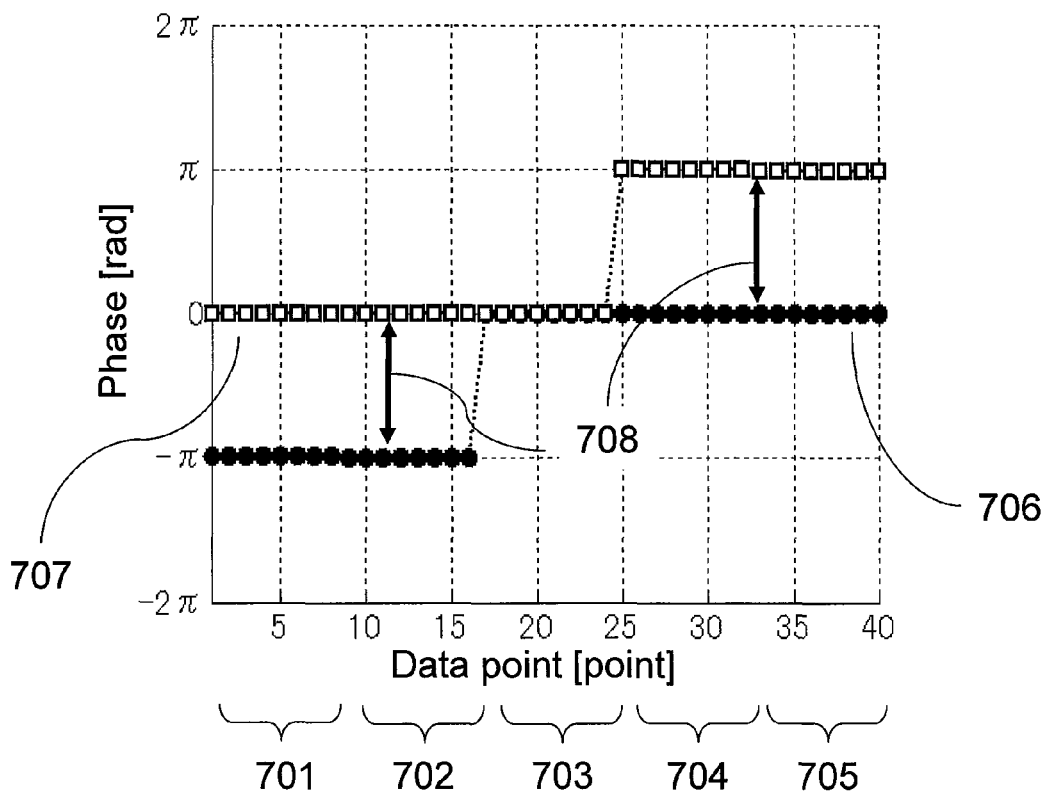
FIG. 7A is a diagram for explaining two of phase maps obtained with the conventional measurement conditions.
Figure 7B:
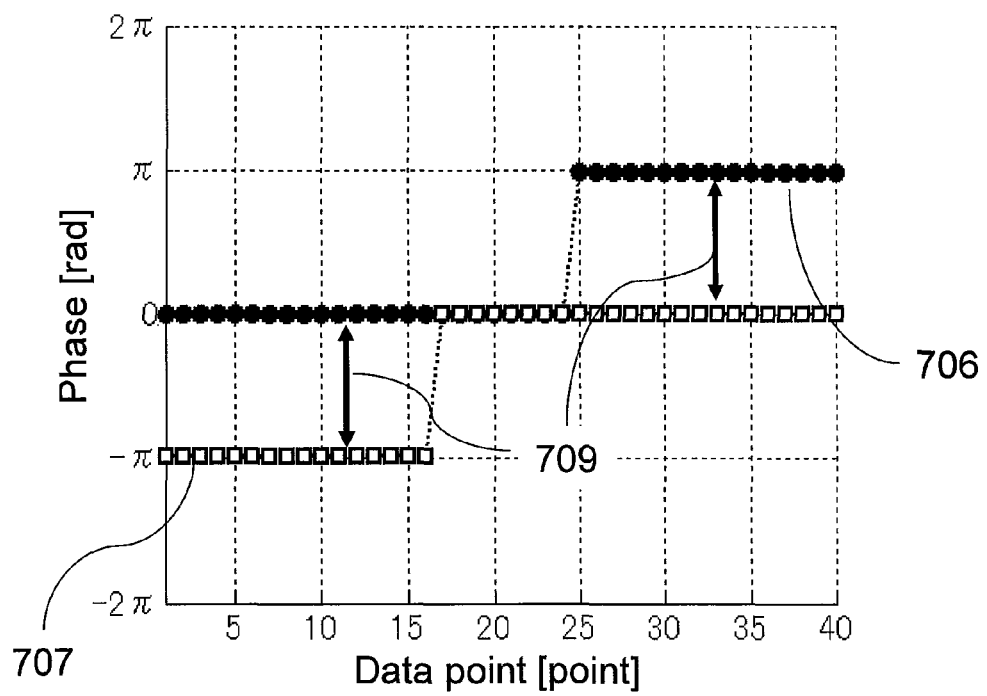
FIG. 7B is a diagram for explaining two of phase maps obtained with the conventional measurement conditions.

Further, the phase maps $\delta_+$ and $\delta_-$ for the condition (C) are shown in FIG. 7A, and the phase maps $\delta_+$ and $\delta_-$ for the condition (D) are shown in FIG. 7B.

In FIG. 6A and FIG. 7A, there are indicated the regions 601 to 605 and 701 to 705, respectively, in which the ratios of water and fat are 0:100, 25:75, 50:50, 75:25, and 100:0. In FIGS. 6 and 7, the black circles 606 and 706 indicate $\delta_+$ for the respective conditions, and the white squares 607 and 707 indicate $\delta_-$ for the respective conditions.

As shown in FIG. 6A, it can be seen that, under the conditions according to this embodiment, the phase difference 608 between $\delta_+$ and $\delta_-$ changes depending on change of the ratio of water and fats. The sudden change of the phase difference 608 between $\delta_+$ and $\delta_-$ depending on change of the ratio of water and fat is called phase jump.

The phase rotation due to inhomogeneity of the static magnetic field spatially changes gradually, so long as there are no magnetic substances such as metals in the neighborhood. Therefore, in a region in which protons continuously exist, phase jump such as the phase difference 608 shown in FIG. 6A does not occur. Therefore, in the regions 601 and 602 in which fats constitute the main component, $\delta_-$ represents the phase rotation due to inhomogeneity of the static magnetic field, and in the regions 604 and 605 in which water constitutes the main component, $\delta_+$ represents the phase rotation due to inhomogeneity of the static magnetic field. In addition, in the region 603, the rates of water and fats are the same, and therefore $\delta_+$ and $\delta_-$ both represent the phase rotation due to inhomogeneity of the static magnetic field.

In addition, as shown in FIG. 6B, when the echo time $t_1$ for the first echo provides out-of-phase state, the phase difference 609 is in an inverse relation with respect to the phase difference 608 shown in FIG. 6A. That is, in the regions 601 and 602 in which fats constitute the main component, $\delta_+$ represents the phase rotation due to inhomogeneity of the static magnetic field, and in the regions 604 and 605 in which water constitutes the main component, $\delta_-$ represents the phase rotation due to inhomogeneity of the static magnetic field.

On the other hand, as shown in FIG. 7A, under the conventional measurement conditions, the phase difference 708 between $\delta_+$ and $\delta_-$ is $\pi$ or $-\pi$ regardless of the ratio of water and fats. Therefore, it cannot be judged which one of regions of $\delta_+$ and $\delta_-$ reflects correct phase rotation.

In addition, as shown in FIG. 7B, when the echo time $t_1$ for the first echo provides the out-of-phase state, the phase difference 709 is in an inverse relation with respect to the phase difference 708 shown in FIG. 7A, as in the case of the phase difference 609 shows in FIG. 6B.

According to this embodiment, in order to distinguish a water image and a fat image, phase jump induced by change of the ratio of water and fats such as the phase difference 608 shown in FIG. 6A and the phase difference 609 shown in FIG. 6B is used.

As described above, the phase rotation induced by inhomogeneity of the static magnetic field spatially changes gradually, so long as there are no magnetic substances such as metals in the neighborhood. Therefore, an arbitrary point in the phase maps $\delta_+$ and $\delta_-$ is used as a reference point, and a point adjacent to the reference point giving the minimum phase difference with respect to the reference point is searched for and calculated with enlarging the region by changing the reference point to finally calculate minimum phase difference maps $\delta_{+1}$ and $\delta_{-1}$. Either one of these minimum phase difference maps $\delta_{+1}$ and $\delta_{-1}$ correctly represents the phase rotation induced by inhomogeneity of the static magnetic field.

The procedures for calculating two of the minimum phase difference maps $\delta_{+1}$ and $\delta_{-1}$ will be explained with reference to FIG. 6A.

[Procedure 1]

The reference point $x_0$ is defined in $\delta_+$ and $\delta_-$. In this case, a point giving the maximum phase difference $|\delta_+ - \delta_-|$ is defined as the reference point $x_0$. For example, the point 610 shown in FIG. 6A is defined as the reference point $x_0$.

[Procedure 2]

In order to calculate the minimum phase difference maps $\delta_{+1}$ and $\delta_{-1}$, values of $\delta_{+1}$ and $\delta_{-1}$ at the reference points $x_0$ are defined. In this case, it is supposed that $\delta_{+1}(x_0)=\delta_+(x_0)$, and $\delta_{-1}(x_0)=\delta_-(x_0)$.

[Procedure 3]

In order to calculate $\delta_{+1}$ and $\delta_{-1}$, for $\delta_{+1}(x_0)$, among the adjacent points $\delta_+(x_0+1)$ and $\delta_-(x_0+1)$, a point giving the minimum phase difference is defined as $\delta_+(x_0+1)$. For example, in FIG. 6A, in the regions 601 and 602, $\delta_+(x_0+1)$ is defined as $\delta_{+1}(x_0+1)$, and in the regions 604 and 605, $\delta_+(x_0+1)$ is defined as $\delta_{+1}(x_0+1)$.

Further, for $\delta_{-1}(x_0)$, among the adjacent points $\delta_+(x_0+1)$ and $\delta_-(x_0+1)$, a point giving the minimum phase difference is defined as $\delta_{-1}(x_0+1)$.

[Procedure 4]

The procedure 3 is repeated until the processing is completed for the whole data to calculate $\delta_{+1}$ and $\delta_{-1}$.

Figure 8:
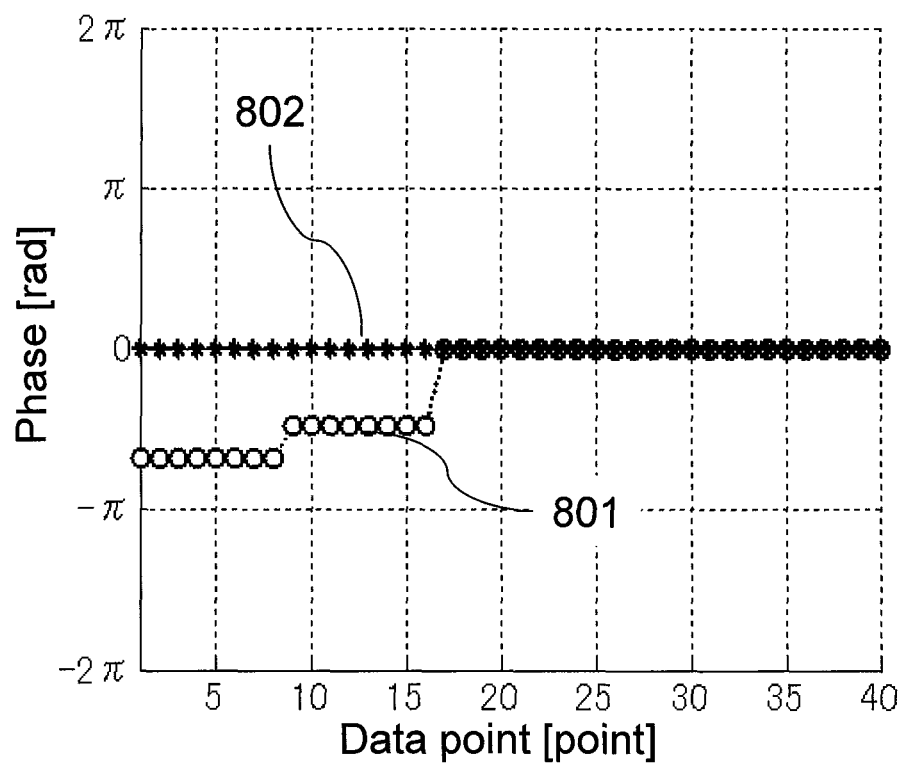
FIG. 8 is a diagram for explaining two of minimum phase difference maps used in the magnetic resonance imaging device according to an embodiment of the present invention.

The minimum phase difference maps $\delta_{+1}$ and $\delta_{-1}$ are shown in FIG. 8. The white circles 801 indicate $\delta_{+1}$, and the asterisks 802 indicate $\delta_{-1}$, respectively. It can be seen that, in each of the minimum phase difference maps $\delta_{+1}$ and $\delta_{-1}$, difference of adjacent points is the minimum difference. Although phase jumps remain in the minimum phase difference map $\delta_{+1}$, they change depending on the position of the reference point $x_0$. In this embodiment, the point 610 shown in FIG. 6A is defined as the reference point $x_0$, and therefore there exist regions where a phase jump remains.

Either one of the two minimum phase difference maps $\delta_{+1}$ and $\delta_{-1}$ obtained above should represent a correct map of phase difference induced by inhomogeneity of the static magnetic field.

Next, among these minimum phase difference maps, the map of phase difference induced by inhomogeneity of the static magnetic field is determined. First, in the step 504 shown in FIG. 5, differential maps $D_+$ and $D_-$ of the two minimum phase difference maps calculated in the step 503 are calculated. Instead of calculating differentials, they may also be obtained by complex division for adjacent points as shown by the equations (27) and (28).

$$D_+(x_{n+1})=\arg(\exp(i\delta_+(x_{n+1}))\cdot\exp(-i\delta_+(x_n))) \quad (27)$$

$$D_-(x_{n+1})=\arg(\exp(i\delta_-(x_{n+1}))\cdot\exp(-i\delta_-(x_n))) \quad (28)$$

In the equations, n represents an integer.

In Step 505 shown in FIG. 5, dispersions in the calculated differential maps $D_+$ and $D_-$ are calculated, and a minimum phase difference map giving the minimum dispersion is chosen. The dispersion may be determined on the basis of values of standard deviation, or judged on the basis of a histogram of differential values by an inspector.

In $\delta_{+1}$ 801 shown in FIG. 8, dispersion of differential values is increased for the phase jumps induced by change of the water and fat ratio. Therefore, the correct phase difference map $\delta$ should be $\delta_{-1}$ 802.

Via the steps described above, the map $\delta$ indicating correct phase difference induced by inhomogeneity of the static magnetic field is calculated.

Hereafter, the method for calculating a phase-corrected image used in Step 514 mentioned above, and the method for calculating a water image and a fat image used in Step 515 will be explained.

An image measured with the first echo is referred to as $I_1$, and an image measured with the second echo is referred to as $I_2$. In Step 514 mentioned above, phase correction of the image $I_2$ is performed by using the phase difference map $\delta$ mentioned above in accordance with the equation (29) to calculate $I_2'$.

$$I_2' = I_2 \cdot \exp(-i\delta) \tag{29}$$

In addition, phase correction of the image $I_1$ may be carried out in accordance with the equation (30) to calculate $I_1'$.

$$I_1' = I_1 \cdot \exp(i\delta) \tag{30}$$

Hereafter, the case where $I_2'$ is calculated and used in Step 514 will be explained as an example.

Then, in Step 515, a water image and a fat image are calculated by using the images $I_1$ and $I_2'$. As described above, if phases of water signal and fat signal at the first echo time are represented as $\sigma_{W1}$ and $\sigma_{F1}$, respectively, phases of water signal and fat signal at the second echo time are represented as $\sigma_{W2}$ and $\sigma_{F2}$, respectively, a water image is represented as W, and a fat image is represented as F, $I_1$ and $I_2'$ can be expressed by the following simultaneous equations.

$$AS = I \tag{31}$$

$$A = \begin{bmatrix} \exp(i\sigma_{W1}) & \exp(i\sigma_{F1}) \\ \exp(i\sigma_{W2}) & \exp(i\sigma_{F2}) \end{bmatrix} \tag{32}$$

$$S = \begin{bmatrix} W \\ F \end{bmatrix} \tag{33}$$

$$I = \begin{bmatrix} I_1 \\ I_2' \end{bmatrix} \tag{34}$$

The equation (33) is transformed by using a transposed matrix $A^t$ and an inverse matrix, and by using the obtained equation (35), a water image and a fat image are calculated.

$$S = (A^t A)^{-1} A^t I \tag{35}$$

The effect of the present invention was confirmed as follows by computer simulation and phantom experiment.

Figure 9A:
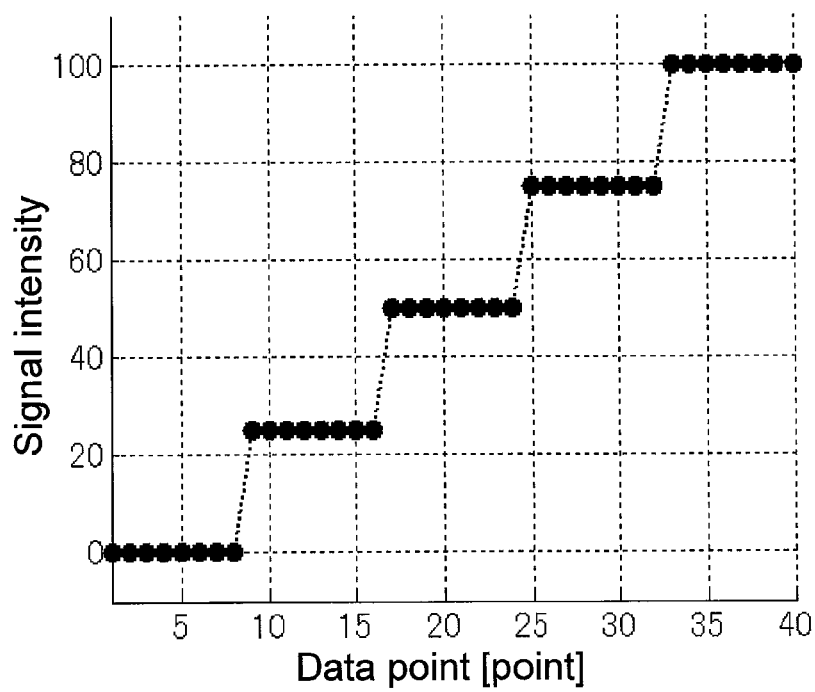
FIG. 9A is a diagram for explaining the effect of the present invention by using results of computer simulation.
Figure 9B:
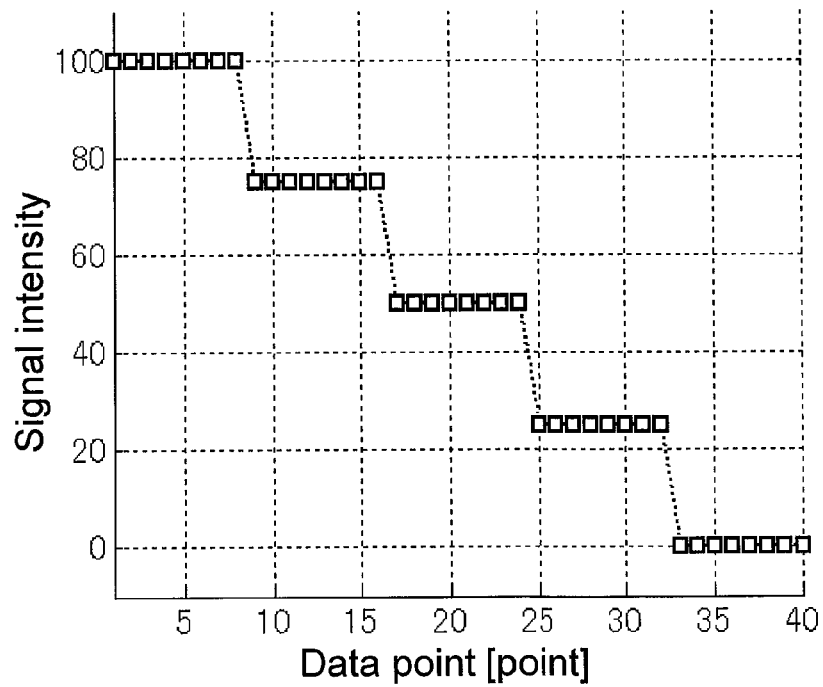
FIG. 9B is a diagram for explaining the effect of the present invention by using results of computer simulation.

The results of the computer simulation are shown in FIG. 9A and FIG. 9B. FIG. 9A shows the results for a water image, and FIG. 9B shows the results for a fat image. The model used in this simulation was the aforementioned model constituted with regions consecutively arranged, in which the ratios of water and fat were 0:100, 25:75, 50:50, 75:25 and 100:0. The first echo time was 4.5 ms, and the second echo time was 6.0 ms.

As shown in FIG. 9A and FIG. 9B, it can be seen that the water image and the fat image could be separated depending on the set water and fat ratios.

The results of the phantom experiment are shown in FIG. 10A, FIG. 10B, FIG. 10C, and FIG. 10D. In FIG. 10A, FIG. 10B, FIG. 10C, and FIG. 10D, there are shown a phantom consisting of nickel chloride aqueous solution 1001, and a fat mat 1002. The measurement conditions consisted of repetition time TR: 80 ms, flip angle: 15 degrees, field of imaging: 360 mm, measurement matrix: 128×128, and number of times of addition: twice.

Figure 10A:
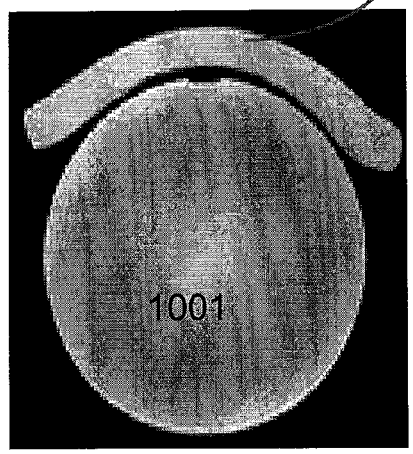
FIG. 10A, shows a result of a phantom experiment for explaining the effect of the present invention.
Figure 10B:
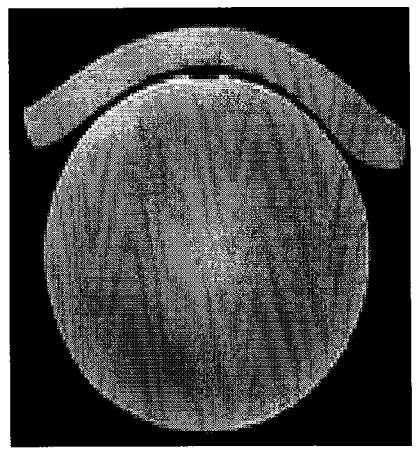
FIG. 10B shows a result of a phantom experiment for explaining the effect of the present invention.
Figure 10C:
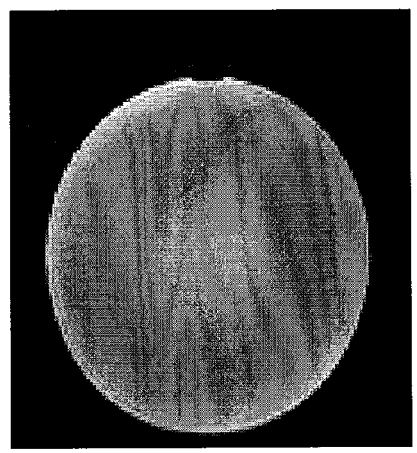
FIG. 10C shows a result of a phantom experiment for explaining the effect of the present invention.
Figure 10D:
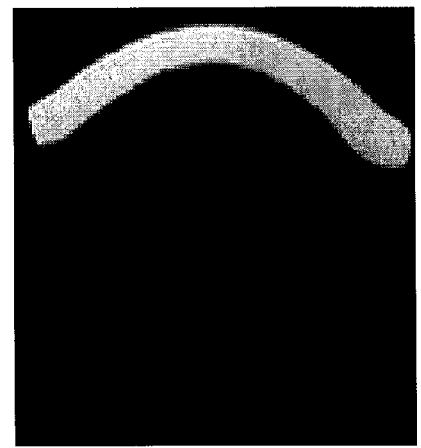
FIG. 10D shows a result of a phantom experiment for explaining the effect of the present invention.

FIG. 10A shows a first echo image measured with an echo time of 4.5 ms, and FIG. 10B shows a second echo image measured with an echo time of 6.0 ms. FIG. 10C and FIG. 10D show the water image and fat image separated according to the present invention, respectively. As shown in FIG. 10C and FIG. 10D, it can be seen that, although the images were not obtained with such echo times that the phases of water and fat signals become in-phase and out-of-phase, respectively, the water image and the fat image could be separated. Moreover, it can be seen that the water image and the fat image were correctly distinguished.

According to the present invention, favorable water/fat separation is realized in water/fat separation imaging, even if the measurement is not performed with such echo times that the phases of water and fat signals become in-phase and out-of-phase as described above. Moreover, it is enabled to determine which is each of the two obtained separation images, a water image or a fat image.

Denotation of Reference Numerals

1: Subject, 2: static magnetic field generation magnet, 3: gradient coil, 4: shim coil, 5: transmission coil, 6: reception coil, 7: transmitter, 8: receiver, 9: computer, 10: display, 11: storage, 12: power supply part for gradient magnetic field, 13: power supply part for shim, 14: sequence control apparatus, 15: input device, 301: RF pulse, 302: read-out gradient magnetic field, 303: first echo, 304: read-out gradient magnetic field, 305: second echo, 401: RF pulse, 402: RF pulse, 403: read-out gradient magnetic field, 404: first echo, 405: read-out gradient magnetic field, 406: second echo, 601: region, 602: region, 603: region, 604: region, 605: region, 606: phase map, 607: phase map, 608: phase difference, 609: phase difference, 610: reference point, 701: region, 702: region, 703: region, 704: region, 705: region, 706: phase map, 707: phase map, 708: phase difference, 709: phase difference, 801: minimum phase difference map, 802: minimum phase difference map, 1001: nickel chloride aqueous solution phantom, 1002: fat mat

The invention claimed is:

1. A magnetic resonance imaging device comprising:
a static magnetic field generation part for generating a static magnetic field in a space in which a subject is placed;
an irradiation part for irradiating a radio frequency magnetic field pulse on the subject;
a reception part for receiving magnetic resonance signals generated from the subject by irradiation of the radio frequency magnetic field pulse;
a gradient magnetic field application part for applying a gradient magnetic field for imparting spatial information to the magnetic resonance signals;
a control part for operating the irradiation part, the gradient magnetic field application part, and the reception part according to a predetermined pulse sequence to perform imaging with two different echo times; and
an image reconstruction part for reconstructing original images from the magnetic resonance signals obtained with the two different echo times,
wherein the image reconstruction part further comprises:
a phase difference map calculation part for calculating phase difference maps induced by inhomogeneity of the static magnetic field from the original images,
a phase-corrected image calculation part for calculating a phase-corrected image by carrying out phase correction of one of the original images using the phase difference map, and
a water/fat separation image calculation part for calculating a water/fat separation image from two images, the phase corrected image and one of the original images not subjected to the phase correction,
wherein the control part further comprises:
an echo time setting part for setting the two different echo times, with each of the echo times selected from among times that the phases of water and fat signals do not become in-phase or out-of-phase, wherein the phase difference map calculation part further comprises:
a water/fat ratio calculation part for calculating water/fat ratios from the original images,
a phase map calculation part for calculating phase maps from the water/fat ratios,
a minimum phase difference map calculation part for searching for a point giving the minimum phase difference for a reference point among adjacent points with enlarging the region to calculate minimum phase difference maps, and
a phase difference map determination part for determining a map of phase difference induced by inhomogeneity of the static magnetic field among the minimum phase difference maps, and
wherein the water/fat ratio calculation part further comprises:
a calculation part for algebraically performing the calculation of the water/fat ratios with a condition that sums of rates of water and fat are constant.

2. A magnetic resonance imaging device comprising:
a static magnetic field generation part for generating a static magnetic field in a space in which a subject is placed;
an irradiation part for irradiating a radio frequency magnetic field pulse on the subject;
a reception part for receiving magnetic resonance signals generated from the subject by irradiation of the radio frequency magnetic field pulse;
a gradient magnetic field application part for applying a gradient magnetic field for imparting spatial information to the magnetic resonance signals;
a control part for operating the irradiation part, the gradient magnetic field application part, and the reception part according to a predetermined pulse sequence to perform imaging with two different echo times; and
an image reconstruction part for reconstructing original images from the magnetic resonance signals obtained with the two different echo times,
wherein the image reconstruction part further comprises:
a phase difference map calculation part for calculating phase difference maps induced by inhomogeneity of the static magnetic field from the original images,
a phase-corrected image calculation part for calculating a phase-corrected image by carrying out phase correction of one of the original images using the phase difference map, and
a water/fat separation image calculation part for calculating a water/fat separation image from two images, the phase corrected image and one of the original images not subjected to the phase correction,
wherein the control part further comprises:
an echo time setting part for setting the two different echo times, with each of the echo times selected from among times that the phases of water and fat signals do not become in-phase or out-of-phase,
wherein the phase difference map calculation part further comprises:
a water/fat ratio calculation part for calculating water/fat ratios from the original images,
a phase map calculation part for calculating phase maps from the water/fat ratios,
a minimum phase difference map calculation part for searching for a point giving the minimum phase difference for a reference point among adjacent points with enlarging the region to calculate minimum phase difference maps, and
a phase difference map determination Dart for determining a map of phase difference induced by inhomogeneity of the static magnetic field among the minimum phase difference maps, and
wherein the water/fat ratio calculation part further comprises:
a calculation part for performing the calculation of the water/fat ratios on the basis of numerical analysis with a condition that sums of rates of water and fats are constant.

3. The magnetic resonance imaging device according to claim 1, wherein:
the phase difference map determination part further comprises:
a selection part for selecting a minimum phase difference map having a minimum standard deviation on the basis of differential values of the minimum phase difference maps.

4. The magnetic resonance imaging device according to claim 2, wherein:
the phase difference map determination part further comprises:
a selection part for selecting a minimum phase difference map having a minimum standard deviation on the basis of differential values of the minimum phase difference maps.

* * * * *